United States Patent [19]

Novak

[11] Patent Number: 5,571,013
[45] Date of Patent: Nov. 5, 1996

[54] INTEGRAL BUR TUBE AND BEARING ASSEMBLY

[75] Inventor: Eugene J. Novak, Deerfield, Ill.

[73] Assignee: Dentsply Research & Development Corp., Milford, Del.

[21] Appl. No.: 221,693

[22] Filed: Mar. 31, 1994

[51] Int. Cl.$^6$ .................................................... A61C 1/05
[52] U.S. Cl. .......................................... 433/132; 433/127
[58] Field of Search ................................. 433/132, 134, 433/135, 120, 127, 128, 129; 415/904

[56] References Cited

U.S. PATENT DOCUMENTS

| | | | |
|---|---|---|---|
| 3,218,109 | 11/1965 | Sato | 415/904 |
| 3,376,084 | 4/1968 | McKee | 433/132 |
| 4,941,828 | 7/1990 | Kimura | 433/132 |
| 5,040,980 | 8/1991 | Heil | 433/127 |

*Primary Examiner*—Cary E. O'Connor
*Attorney, Agent, or Firm*—James B. Bieber

[57] ABSTRACT

A dental handpiece includes a head, a tubular chuck having an open-end axial bore for receiving the shank of a dental bur and a tubular bur tube having an outer surface and an axial bore therethrough for receiving the chuck therein. The bur tube has at least one inner raceway formed integrally along its outer surface. An outer race having an outer raceway is associated with the inner raceway. A plurality of ball bearings are mounted between the raceways. A rotor may be formed integrally with the outer surface of the bur tube.

15 Claims, 1 Drawing Sheet

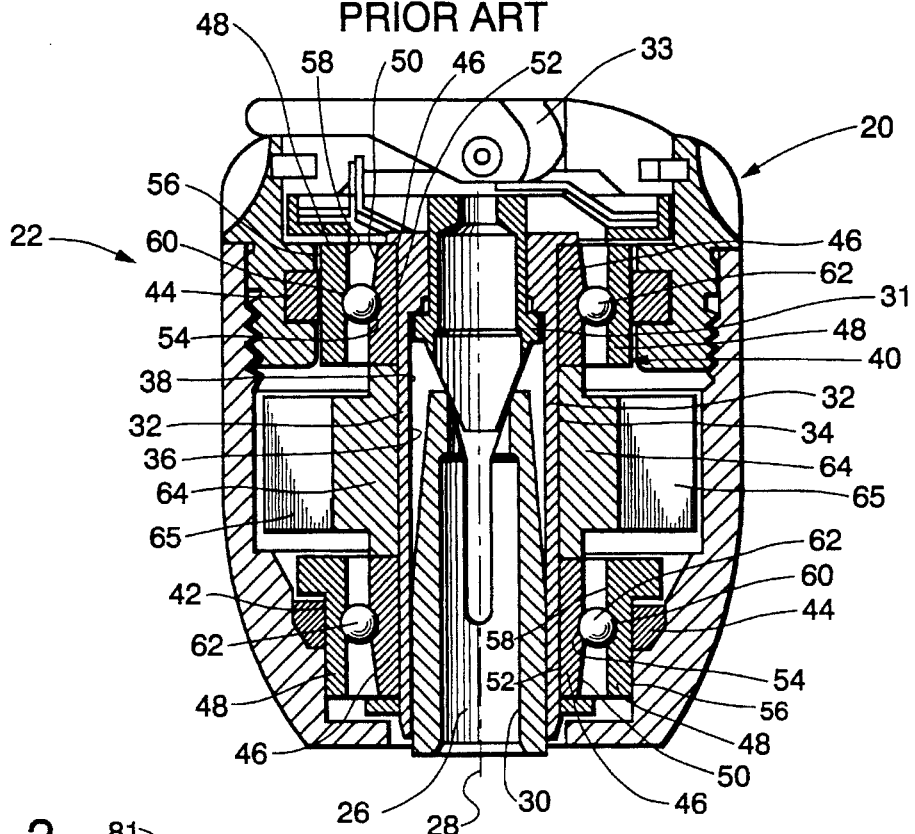

INTEGRAL BUR TUBE AND BEARING ASSEMBLY

FIELD OF THE INVENTION

This invention is generally directed to an improved bur tube or rotor tube for a dental handpiece.

BACKGROUND OF THE INVENTION

A bur tube, such as the one found in U.S. Pat. No. 5,040,980 entitled Dental Handpiece with Spring Grip Chuck and Lever Release Mechanism, is used in a dental handpiece in connection with a chuck to mount a dental bur, i.e., a drill bit or cutting tool. Normally, the bur or cutting tool is held within the chuck which is, in turn, held within the bur tube.

The bur tube is a relatively thin, small diameter tubular member having a slightly tapered outer surface. Ball bearing assemblies mount the bur tube within the head of the dental handpiece. A rotor is mounted on the bur tube and rotates the bur tube and consequently the bur or cutting tool in response to an air stream which is fed through the handpiece. Conventional rotational speeds are very high, on the order of 400,000 rpm. The parts of the dental handpiece must be carefully made, selected and assembled to assure both proper "in round" and balance for vibration free or "true" rotation at this speed.

Heretofore, a pair of bill bearing assemblies (bearings) have been pressed directly over the outer surface of the bur tube itself. These bearings rotatably mount the bur tube to an inside surface of the head of the handpiece. If the bearings are too loose, the bur tube will be out of balance and cause excessive vibration and premature wear of the parts. If the bearings are too tight, the bearings tend to distort the bur tube causing an "out-of-round" configuration and interfering with proper rotation at high speeds which can lead to premature failure.

The rotor has also been pressed directly over the outer surface of the bur tube. As with the abovedescribed problems that exist when the bearing assemblies are press fit, certain problems occur when the rotor is press fit over the outer surface of the bur tube. That is, if the rotor is too loose, the rotor will slip relative to the bur tube and fail to rotate the bur tube properly. If the rotor is too tight, the rotor tends to distort the bur tube and interferes with proper rotation at high speeds which can lead to premature failure.

The present invention is intended to avoid the foregoing method of assembly and attendant problems.

OBJECTS AND SUMMARY OF THE INVENTION

A general object of the present invention is to provide a novel and improved bur tube to be mounted within a head of a dental handpiece by ball bearing assemblies.

A more particular object of the present invention is to provide a bur tube that eliminates the need to press fit bearings over the outer surface of the bur tube.

An object of the present invention is to provide a bur tube that does not require bearings to be selectively sized and fitted to the bur tube.

Briefly, and in accordance with the foregoing, the present invention comprises an improved bur tube and bearing assembly for use with a dental handpiece which includes a head and a tubular chuck having an open-ended axial bore for receiving the shank of a dental bur therein. The bur tube is generally tubular, having an outer surface and an axial bore therethrough for receiving the chuck therein. The bur tube has at least one inner raceway formed integrally along its outer surface.

In accordance with another aspect of the invention, a rotor may be formed integrally with the outer surface of the bur tube.

BRIEF DESCRIPTION OF THE DRAWINGS

The features of the present invention which are believed to be novel are set forth with particularity in the appended claims. The organization and manner of operation of the invention, together with further objects and advantages thereof, may best be understood by reference to the following description taken in connection with the accompanying drawings in which like references numerals identify like elements, and in which:

FIG. 1 is a sectional view of a head of a prior art dental handpiece;

FIG. 2 is a sectional view of a portion of a head of a dental handpiece which includes a bur tube according to a first embodiment of the present invention; and FIG. 3 is a sectional view of a portion of a head of a dental handpiece which includes a bur tube according to a second embodiment of the present invention.

DETAILED DESCRIPTION OF THE PREFERRED EMBODIMENT

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

Referring initially to FIG. 1, a head 20 of a conventional prior art dental handpiece 22, as found in U.S. Pat. No. 5,040,980 entitled Dental Handpiece with Spring Grip Chuck and Lever Release Mechanism, is shown. The head 20 of the dental handpiece 22 is connected to an elongate handle (not shown). The disclosure of U.S. Pat. No. 5,040,980 is herein incorporated by reference.

A tubular chuck 26 is to be mounted so as to be located along a center line 28 of the head 20. The chuck 26 has an axial bore 30 therethrough and mounts a dental bur (i.e. drill bit or cutting tool-not shown).

A bur tube or rotor tube 32 is used in the dental handpiece 22 to mount the chuck 26. The bur tube 32 is a relatively thin, small diameter tubular member having a slightly tapered outer surface 34 and an inner surface 36 defined by an axial bore 38. The bur tube 32 is made of a suitable high strength, long lasting material, such as a hardened stainless steel. The dental bur is releasably held in the axial bore 30 of the chuck 26 and the chuck 26 is in turn press fit into the axial bore 38 of the bur tube 32. In some constructions, the chuck is threaded into the bur tube. The particular form of the chuck and its method of assembly with the bur tube may take other forms without departing from the invention.

The bur tube 32 is mounted for rotation within the head 20 of the dental handpiece 22 by an upper bearing assembly 40 and a lower bearing assembly 42. Resilient rings 44 support the bearings assemblies 40, 42 within the head 20.

Each bearing assembly 40, 42 includes an inner race 46 and an outer race 48 associated therewith. Each inner race 46 is an annular member having a radially outer surface 50 and a radially inner surface 52 defining an axial bore. An annular groove or raceway 54 is formed along the outer surface 50. The outer race 48 is an annular member having a radially outer surface 56 and a radially inner surface 58. A groove or raceway 60 is formed along the inner surface 58. A plurality of ball bearings 62 are mounted between the inner race 46 and the outer race 48 positioned between the raceways 54, 60. The outer surface 56 of each outer race 48 abuts one of the resilient rings 44.

To mount the bearing assemblies 40, 42 onto the bur tube 32, each bearing assembly 40, 42 is press fit over the outer surface 34 of the bur tube 32. Thus, the inner surface or axial bore 52 of each inner race 46 fits snugly against the outer surface 34 of the bur tube 32. As discussed hereinabove, if the bearing assemblies 40, 42 are too loose, the bur tube 32 will be out of balance and cause excessive vibration and premature wear of the parts. If the bearing assemblies 40, 42 are too tight, they tend to distort the bur tube 32 and interfere with proper rotation at high speeds which can lead to premature failure.

A rotor or turbine 64 is also mounted along the outer surface 34 of the bur tube 32. Conventionally, the rotor 64 is press fit over the outer surface 34 of the bur tube 32. The rotor 64 rotates the bur tube 32 and consequently the cutting tool in response to an air stream which is fed through the handpiece 22 and impinges against the blades 65 of the rotor 64.

Turning now to the present invention, a first embodiment of an improved bur tube 70 is shown in FIG. 2 and will be described. The bur tube 70 is used in a head of a dental handpiece such as the one shown in FIG. 1. For clarity, the surrounding features of the head of the dental handpiece are not repeated in FIG. 2.

The bur tube 70 is a relatively small diameter tubular member having an outer surface 72 and an inner surface 74 defining an axial bore 76. The outer surface 72 of the bur tube 70 may have tapered end portions 78. By way of example, the outside diameter of the bur tube 70 may be approximately 0.15 inches and the inside diameter may be approximately 0.10 inches. It will be noted that the wall thickness of the bur tube 70 is somewhat greater than that of the bur tube 30 of FIG. 1, to allow for the formation of raceways 90 thereon, as will be further described hereinbelow. The bur tube 70 is made of a suitable high strength, long lasting material, such as a hardened stainless steel.

The bore 76 of the bur tube 70 is located along an axis or center line 81 of the head of the dental handpiece. The bore 76 mounts a conventional chuck (not shown) which in turn may receive a dental bur (i.e. drill bit or cutting tool-not shown). The chuck used in the improved bur tube 70 may be substantially similar to the chuck 26 of FIG. 1. An increased diameter bore portion 80 and decreased diameter bore portion 82 may be provided on axis 81 for accommodating a mechanism, similar to that indicated in FIG. 1 by reference numerals 31, 33 for gripping and releasing a bur in a chuck similar to chuck 26.

The bur tube 70 is mounted for rotation within the head of the dental handpiece by an upper bearing assembly 84 and a lower bearing assembly 86. Resilient rings (not shown) much like the rings 44 of FIG. 1 may be used to support the bearing assemblies 84, 86 within the head for reducing noise levels and attenuating vibration during the operation of the handpiece.

Each bearing assembly 84, 86 includes an annular inner groove or raceway 90 and an outer race 92 associated therewith. Each outer race 92 is an annular member having an outer surface 94 and an inner surface 96. Each inner surface 96 has an annular raceway or groove 98 formed thereon.

In accordance with one aspect of the invention, the inner raceway 90 is integrally formed along the outer surface 72 of the bur tube 70 when the bur tube 70 is manufactured. The inner raceways 90 are axially spaced from each other along the length of the bur tube 70.

The formation of the inner raceways 90 integrally with the bur tube 70 eliminates the need to press fit the inner races of independent bearings over the bur tube as was done in prior art assemblies. This also eliminates separate inner races, which permits the above-noted thicker walled construction of the bur tube 70 to accommodate raceways 90 while maintaining the same outer diameter overall of the bearing assemblies 84, 86 as for bearing assemblies 40, 42 of FIG. 1. Thus, bearing assemblies 84, 86 can be provided with outer diameters which will interfit with the same rings 44 without altering any other part of the head assembly as shown in FIG. 1. Also, the inner diameter of bore 76 may be maintained the same as that of the bore 36 for accommodating a chuck of the same outer diameter in the chuck 26 of the prior art assembly. That is, the increase in thickness adds only to the outer diameter of the bur tube.

A plurality of ball bearing elements or balls 100 are placed between the raceways 90, 98. The manufactured size of each inner raceway 90 is of a predetermined configuration which corresponds to the size of the ball bearing 100 that is to be used. Because the end portions 78 are tapered, the outer races 92 and balls 100 are readily mounted onto the bur tube 70, i.e., each ball 100 can roll along the tapered end portions 78 until it reaches the inner raceway 90. Moreover, since the inner raceways 90 are integrally formed along the outer surface 72 of the bur tube 70, the need to individually size, select and fit a ball bearing assembly to the bur tube is eliminated. Furthermore, since the inner raceways 90 are integrally formed on the bur tube 70, each bearing assembly 84, 86 is in a predetermined location and an improved geometrical relationship between the ball bearing elements 100 and the center line 81 of the head of the dental handpiece is achieved.

Each bearing assembly 84, 86 may also include a bearing retainer or cage piece 102. The bearing retainer 102 surrounds the ball bearing elements 100 to keep the ball bearing elements 100 evenly spaced.

A rotor or turbine 104 rotates the bur tube 70 and consequently the cutting tool in response to an air stream which is fed through the handpiece and impinges upon its blades 105. As shown in FIG. 2, the rotor or turbine 104 may be formed as a separate piece and press fit over the outer surface 72 of the bur tube 70 in manner similar to which was done in the above-described prior art dental handpiece. The rotor 104 is located along a midsection 106 of the bur tube 70, between the bearing assemblies 84, 86.

A bur tube 170 and bearing assemblies 84, 186, as shown in FIG. 3, are similar to the bur tube 70 and bearing assemblies 84, 86 as shown in FIG. 2. The elements in FIG. 3 indicated by the reference numbers 181, 182, 192, 196 and 198 correspond to equivalent elements in FIG. 2 having reference numbers 81, 82, 92, 96 and 98, respectively. As such, only the more significant differences will be described. The similar parts and components are designated by similar reference numerals to those used in FIG. 2 but greater by 100.

The bur tube 170 is a relatively small diameter tubular member having an outer surface 172 and an inner surface 174 defining an axial bore 176. The bur tube 170 has end portions 178 that have an outer diameter which is smaller than the outer diameter of a midsection 206 of the bur tube 170. Grooves or raceways 190 are integrally formed along the outer surface 194 of the bur tube 170 at the areas where the end portions 178 adjoin the midsection 206. By having this configuration, the bearing assemblies 84, 186 are easily mounted onto the bur tube 170 since each ball bearing element 100 can roll along the end portions 178 until the bearing element 100 contacts the raceway 190.

As shown in FIG. 3, the rotor or turbine 204 may be integrally formed as part of the bur tube 170. This eliminates the need to press fit the rotor over the outer surface of the bur tube and eliminates the problems associated with sizing, selection and assembly of a rotor. It is to be understood that the bur tube 70 shown in FIG. 2 may also have a rotor integrally formed therewith. Alternatively, it is to be understood that the bur tube 170 shown in FIG. 3 may have a rotor press fit thereon.

While particular embodiments of the invention have been shown and described in detail, it will obvious to those skilled in the art that changes and modifications of the present invention, in its various aspects, may be made without departing from the invention in its broader aspects, some of which changes and modifications being matters of routine engineering or design, and others being apparent only after study. As such, the scope of the invention should not be limited by the particular embodiments and specific constructions described herein but should be defined by the appended claims and equivalents thereof. Accordingly, the aim in the appended claims is to cover all such changes and modifications as fall within the true spirit and scope of the invention.

The invention claimed is:

1. An improved dental handpiece having a head containing an air driven rotor that is supported therein by at least one bearing assembly including an outer race in contact with said head and an outer raceway for retaining bearing elements for supporting and positioning said rotor, said handpiece comprising:

a bur tube supporting said rotor in said head, said tube having outer cylindrical surfaces and an axial bore for receiving and retaining a dental bur, at least one end of said bur tube including a tapered portion and having at least one bearing inner raceway formed in said tapered outer surface portion, said taper and raceway arranged such that, in combination with said outer race and raceway, axial advancement of said bearing assembly upon assembly is limited to a predetermined geometrical relationship.

2. A bur tube as defined in claim 1, wherein said bur tube has a pair of inner raceways formed integrally therewith and axially spaced apart along said outer surface.

3. A bur tube as defined in claim 2, wherein said outer surface includes a midsection and end portions, said end portions being of a smaller diameter than said midsection and adjoining said midsection portion, said raceways being formed adjacent where said end portions adjoin said midsection portions.

4. A bur tube as defined in claim 3, wherein said inner raceways are formed where said end portions adjoin said midsection.

5. A bur tube as defined in claim 1, wherein said bur tube further includes a rotor integrally formed therewith along said outer surface.

6. An improved handpiece including a bur tube and bearing assembly for use with a dental handpiece having a head and a tubular chuck having an axial bore for receiving the shank of a dental bur; said assembly comprising:

a bur tube having an outer cylindrical surfaces and an axial bore therethrough for receiving a chuck therein, said bur tube including at least one tapered outer surface end portion having at least one raceway formed integrally therewith;

at least one outer race, having an outer raceway formed complementary to said inner raceway; and a plurality of ball bearing elements engaged between the inner and outer raceways, said taper and outer race dimensioned to limit axial advancement of said bearing assembly on said bur tube outer surfaces just until said ball bearing elements are positioned in said inner and outer raceways.

7. A bur tube and bearing assembly as defined in claim 6, wherein said tube further includes a rotor intergrally formed therewith along said outer surface.

8. A bur tube and bearing assembly as defined in claim 6, further including a rotor attached to said bur tube along said outer surface.

9. A bur tube and bearing assembly as defined in claim 6, further including bearing retainers around said ball bearings.

10. A bur tube and bearing assembly as defined in claim 6, wherein said outer surfaces include a second tapered end portion at the opposite end of said bur tube.

11. A bur tube and bearing assembly as defined in claim 10, wherein said bur tube has a second inner raceway formed integrally therewith and axially spaced apart from said one inner raceway along said outer surface in the opposite tapered portion; and further including a second outer race having a second outer raceway complementary to said second inner raceway and a second plurality of ball bearing elements engaged between said second inner and second outer raceways.

12. A bur tube and bearing assembly as defined in claim 11, wherein a rotor is intergrally formed along side outer surface between said two intergrally formed inner raceways.

13. A bur tube and bearing assembly as defined in claim 11, wherein a rotor is press fit over the outer surface of said bur tube between said inner raceways.

14. A bur tube and bearing assembly as defined in claim 11, wherein said outer surface includes a midsection and end portions, said end portions being of a smaller diameter than said midsection portion and adjoining said midsection portion, said raceways being formed adjacent where said end portions adjoin said midsection portions.

15. A bur tube and bearing assembly as defined in claim 14, wherein said inner raceways are formed where said end portions adjoin said midsection.

* * * * *